United States Patent
McKibben

(10) Patent No.: US 8,192,757 B2
(45) Date of Patent: Jun. 5, 2012

(54) COMPOSITIONS AND METHODS FOR ATTRACTING NOCTUID MOTHS

(75) Inventor: Gerald H. McKibben, Starkville, MS (US)

(73) Assignee: Cotton Incorporated, Cary, NC (US)

(*) Notice: Subject to any disclaimer, the term of this patent is extended or adjusted under 35 U.S.C. 154(b) by 832 days.

(21) Appl. No.: 11/774,390

(22) Filed: Jul. 6, 2007

(65) Prior Publication Data

US 2008/0044446 A1   Feb. 21, 2008

Related U.S. Application Data

(60) Provisional application No. 60/830,653, filed on Jul. 12, 2006.

(51) Int. Cl.
- *A01N 37/16* (2006.01)
- *A01N 25/28* (2006.01)
- *A01N 25/34* (2006.01)
- *A01N 31/02* (2006.01)
- *A01M 1/20* (2006.01)

(52) U.S. Cl. .............. 424/480; 424/84; 43/107

(58) Field of Classification Search .............. None
See application file for complete search history.

(56) References Cited

U.S. PATENT DOCUMENTS

| | | | |
|---|---|---|---|
| 5,665,344 A | 9/1997 | Pair et al. | |
| 6,183,733 B1 * | 2/2001 | McKibben | 424/84 |
| 6,190,652 B1 | 2/2001 | Pair et al. | |
| 6,316,017 B1 | 11/2001 | McKibben et al. | |
| 6,773,727 B1 | 8/2004 | Rojas et al. | |
| 2008/0044446 A1* | 2/2008 | McKibben | 424/408 |

FOREIGN PATENT DOCUMENTS

WO   WO 01/28327   4/2001

OTHER PUBLICATIONS

Gogi et al. (Pest Management Science. 2006; 62: 982-990).*
Nakagawa (Journal of Pesticide Science. 2007; 32 (2): 135-136).*
Minakuchi et al. (Journal of Pesticide Science. 2006; 31 (2): 77-84).*
Dickens et al. (Journal of Insect Physiology. 1993; 39 (6): 503-516).*
Showler et al. (Journal of Economical Entomology. 2005; 98 (2): 373-377), provided in IDS.*
Hillier et al. (Journal of Comparative Physiology. 2006; 192: 199-219).*
Mitchell et al. (Florida Entomologist Online. 1994; 77 (2): 237-247.*
Showler, A.T. et al., "Effect of aging on pheromone emission from a commercial beet armyworm (Lepidoptera: Noctuidae) lure and trap efficiency." J. Econ. Entomol. (2005) vol. 98 (2), pp. 373-377.
Lopez, J.D., Jr., "Evaluation of some commercially available trap designs and sex pheromone lures for *Spodoptera exigua* . . . " J. Econ. Entomol. (1998) vol. 91(2), pp. 517-521.

(Continued)

*Primary Examiner* — Shanon A Foley
(74) *Attorney, Agent, or Firm* — SNR Denton US LLP

(57) ABSTRACT

The invention provides compositions for attracting noctuid moths, which include at least one pheromone and at least one synergist. The synergist is a naturally-occurring phytochemical compound. The synergist is preferably β-caryophyllene, iso-caryophyllene, α-humulene, or combinations thereof. The invention also provides traps containing the composition for attracting noctuid moths, and methods for attracting, capturing, killing or sterilizing noctuid moths using the composition.

34 Claims, 4 Drawing Sheets

OTHER PUBLICATIONS

Lopez, J.D., Jr., "Evaluation of various operational aspects for sex pheromone trapping of beet armyworm." Southwestern Entomologist (1998) vol. 23(4), pp. 301-307.

Parajulee, M.N. et al., Long-term seasonal abundance patterns of *Helicoverpa zea* and *Heliothis virescens* (Lepidoptera: Noctuidae) in the Texas high plains. J. Econ. Entomol. (2004) vol. 97(2), pp. 668-677.

Parajulee, M.N. et al., "Seasonal activitiy of *Helicoverpa zea* and *Heliothis virescens* (Lepidoptera: Noctuidae) detected by . . . " Environ. Entomol. (1998) vol. 27(5), pp. 1203-1219.

Lopez, J.D., Jr., "Comparison of two sex pheromone trap designs for monitoring corn earworm and tobacco budworm . . . " J. Econ. Entomol. (1994) vol. 87(3), pp. 793-801.

* cited by examiner

COMPOSITIONS AND METHODS FOR ATTRACTING NOCTUID MOTHS

RELATED APPLICATIONS

This application claims priority to provisional U.S. application No. 60/830,653, filed Jul. 12, 2006, the contents of which are incorporated by reference herein in their entirety.

FIELD OF THE INVENTION

The invention is directed to novel compositions and methods using these novel compositions for attracting moths, particularly noctuid moths.

BACKGROUND OF THE INVENTION

Noctuid moths including beet armyworm, corn earworm, and tobacco bud worm are pests which attack several economically important crops, including cotton. Although a variety of chemical pesticides have been used in the past to control noctuid moths, there are serious disadvantages in these pesticides. Some pesticides pollute the environment while others are toxic to humans. Such environmental and consumer safety concerns have led to the deregistration of many pesticides. Also, there is generally a reluctance to use any pesticides on agricultural products which are consumed as food. Therefore, eliminating, or at least reducing the amount of toxic pesticides used in the management of insect pests is desirable. Consequently, scientists have pursued the development of alternative pest control agents that are safer for the environment and for consumers. Among such alternative control agents are insect sex pheromones.

Many insects communicate by releasing volatile pheromones. Sex pheromones, for example, are typically released by one sex at appropriate times to attract the other sex of the same species. This phenomenon has been exploited to trap the insects of one sex and kill them, thereby preventing mating and reducing the insect population in following generations. Pheromones have been used in this way on a commercial basis for several years, and provide effective control of numerous insect pest species including noctuid moths.

Although the use of pheromones is advantageous, most pheromones are artificially synthesized, and thus are very expensive. As a result, pest control or pest management using synthetic pheromones is not always cost efficient. In some cases, naturally occurring and less-expensive compounds can be identified that act as synergists to synthetic pheromones. For example, eugenol, a naturally occurring compound, has been identified as a synergist and is used with the synthetic pheromone, grandlure, for capturing and controlling cotton boll weevils. The naturally-occurring compound adds to the attractant effect of the grandlure (McKibben et al., U.S. Pat. No. 6,183,733).

To date, no such synergists, have been identified for pheromones of noctuid moths. Accordingly, there exists a need to identify synergists for noctuid-moth-pheromones and develop less-expensive attractant formulations.

SUMMARY OF THE INVENTION

The invention provides synergists for noctuid-moth-pheromones, and attractant-compositions for attracting noctuid moths, which comprise pheromones and synergists. The attractant-composition attracts insects of one or more species of the family Noctuidae including, but not limited to, beet army worm and tobacco bud worm.

The attractant-compositions contain at least one pheromone and at least one synergist for attracting noctuid moths. In preferred embodiments, the pheromone is selected from the group (Z,E)-9,12-tetradecadien-1-ol acetate, (Z)-9-tetradecen-1-ol acetate and (Z)-11-hexadecen-1-ol, and combinations thereof and the synergist is selected from the group β-caryophyllene, iso-caryophyllene and α-humulene, and combinations thereof. In some embodiments, the attractant-composition further contains one or more additives such as, for example, pesticides, insect sterilants and/or insect growth regulators. The attractant-compositions may incorporate inert additives and carriers, and be in the form of a liquid, pellets, microspeheres, nanoparticles, tubules or combinations thereof.

The invention provides traps for capturing noctuid moths, which include one or more septa or containers for holding the attractant-composition.

The invention also provides a method for attracting and trapping noctuid moths, thereby protecting crop plants from noctuid moths. The method comprises the steps of attracting noctuid moths with an attractant-composition of the invention; trapping the noctuid moths; and killing or sterilizing the trapped noctuid moths. Crop plants protected in this manner include, but are not limited to, cotton, corn, tobacco, soybean, tomato, artichoke, asparagus, cabbage, cantaloupe, collard, cowpea, cucumber, eggplant, lima bean, melon, okra, pea, pepper, potato, pumpkin, snap bean, spinach, squash, sweet potato, lettuce, alfalfa, flax, oat, millet, rice, sorghum, sugarcane, sunflower, vetch, and wheat and okra.

In some embodiments, the method may include an additional step of assessing the population of trapped noctuid moths. Such assessments may help, periodically, to monitor the noctuid moth population in a crop field.

Other features and advantages of the present invention will become apparent from the following detailed description. It should be understood, however, that the detailed description and the specific examples, while disclosing the preferred embodiments of the invention, are given by way of illustration only, and that various changes and modifications apparent to those skilled in the art are within the spirit and scope of the invention and the appended claims.

DETAILED DESCRIPTION OF THE INVENTION

Figure 1:
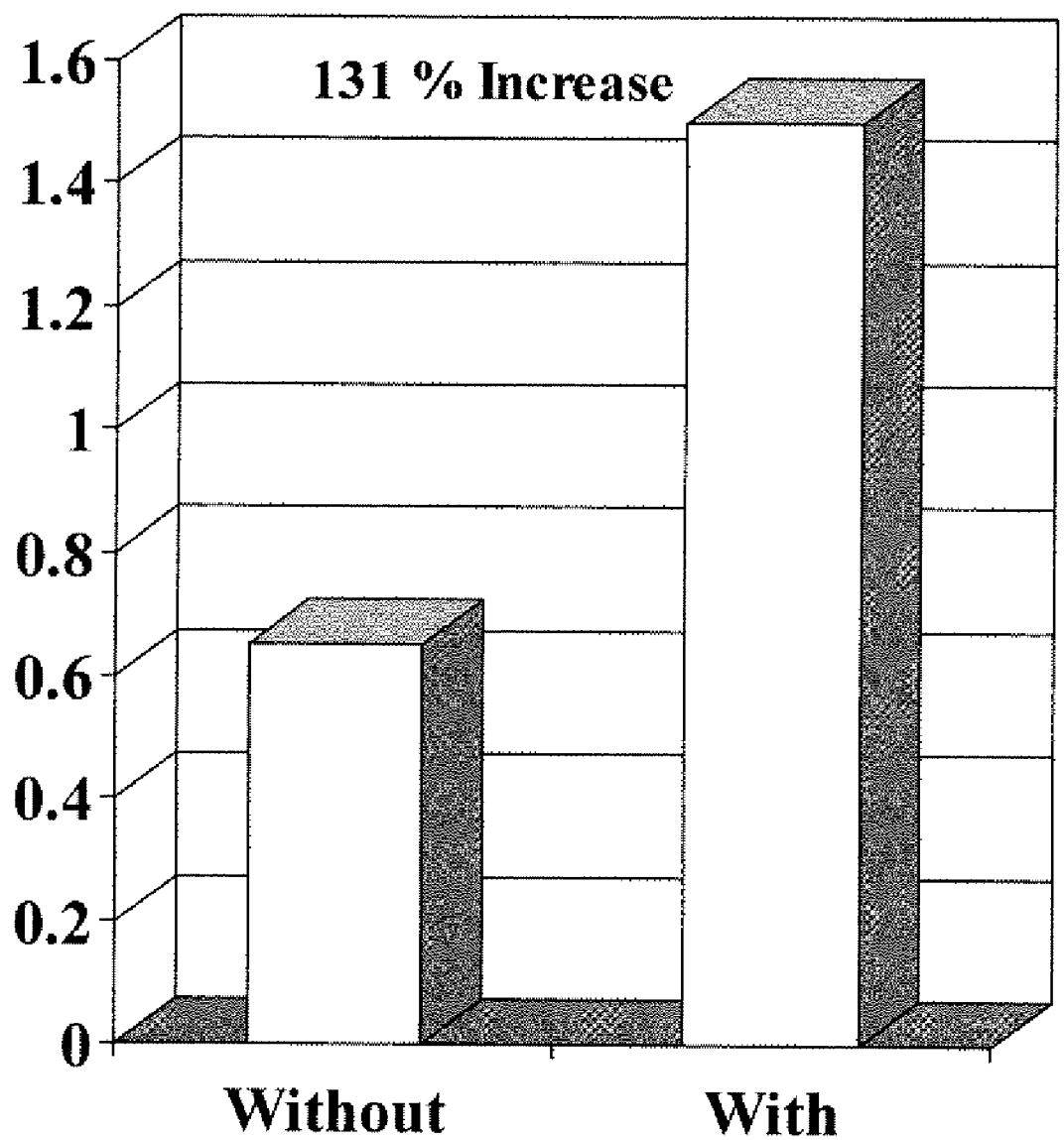
FIG. 1 illustrates a response of *Heliothis virescens* in a cotton environment to pheromone compositions with and without β-caryophyllene as a synergist in year 2005.

The attractant-compositions of the invention contain at least two compounds. The first compound is a pheromone and the second compound is a synergist, as defined herein. The term "pheromone," as used herein, means a volatile chemical or a set of volatile chemicals that attract at least one species of noctuid moth.

In some embodiments, the pheromone is a sex pheromone which attracts one sex of a noctuid moth. In particular embodiments, the pheromone is selected from the group (Z,E)-9,12-tetradecadien-1-ol acetate, (Z)-9-tetradecen-1-ol acetate and (Z)-11-hexadecen-1-ol, and combinations thereof. In one embodiment, the pheromone for attracting beet army worm is a mixture of (Z,E)-9,12-tetradecadien-1-ol acetate and (Z)-9-tetradecen-1-ol acetate, preferably, in a ratio of 7:3. In another embodiment, the pheromone for attracting tobacco bud worm is (Z)-11-hexadecen-1-ol or its isomer. The pheromone may be naturally occurring or chemically synthesized by methods known to one skilled in the art.

The term, "synergist," as used herein, refers to a substance that can be used with a noctuid-moth-pheromone for reducing the amount of the pheromone dose or enhancing the effectiveness of the pheromone for attracting at least one species of noctuid moth. The synergist may or may not be an independent attractant of noctuid moths in the absence of a pheromone.

In preferred embodiments, the synergist is a volatile phytochemical that attracts at least one species of noctuid moth. The term, "phytochemical," as used herein, means a compound occurring naturally in a plant species.

In a particular embodiment, the synergist is selected from the group comprising β-caryophyllene, iso-caryophyllene and α-humulene, and combinations thereof. In a preferred embodiment, the synergist is β-caryophyllene or its Z isomer.

The attractant-composition may contain the pheromone and the synergist in a mixed or otherwise combined form or it may contain the pheromone and the synergist independently in a non-mixed form.

The attractant-compositions may include one or more insecticides. In one embodiment, the insecticides are chemical insecticides known to one skilled in the art. Examples of the chemical insecticides include one or more of pyrethoroid or organophosphorus insecticides, including but are not limited to, cyfluthrin, permethrin, cypermethrin, bifinthrin, fenvalerate, flucythrinate, azinphosmethyl, methyl parathion, and malathion.

In another embodiment, the insecticides are one or more biological insecticides known to one skilled in the art. Examples of the biological insecticides include, but are not limited to, toxins from natural pyrethrins, *Bacillus thuringiencis* and *Beauveria bassiana*.

In certain embodiments, the attractant-composition may include one or more polymeric agents known to one skilled in the art. The polymeric agents may control the rate of release of the composition to the environment. In some embodiments, the polymeric attractant-composition is impervious to environmental conditions. The polymeric agent may also be a sustained-release agent that enables the composition to be released to the environment in a sustained manner.

Examples of polymeric agents include, but are not limited to, celluloses, proteins such as casein, fluorocarbon-based polymers, hydrogenated rosins, lignins, melamine, polyurethanes, vinyl polymers such as polyvinyl acetate (PVAC), polycarbonates, polyvinylidene dinitrile, polyamides, polyvinyl alcohol (PVA), polyamide-aldehyde, polyvinyl aldehyde, polyesters, polyvinyl chloride (PVC), polyethylenes, polystyrenes, polyvinylidene, silicones, and combinations thereof Examples of celluloses include, but are not limited to, methylcellulose, ethyl cellulose, cellulose acetate, cellulose acetate-butyrate, cellulose acetate-propionate, cellulose propionate, and combinations thereof.

According to another embodiment of the invention, the attractant-composition may include one or more insect feeding stimulants. Examples of insect feeding stimulants include, but are not limited to, crude cottonseed oil, fatty acid esters of phytol, fatty acid esters of geranyl geraniol, fatty acid esters of other plant alcohols, plant extracts, and combinations thereof.

According to another embodiment of the invention, the attractant-composition may include one or more insect growth regulators ("IGRs"). IGRs may be used to alter the growth of the noctuid moths and produce deformed noctuid moths. Examples of insect growth regulators include, for example, dimilin.

According to another embodiment of the invention, the attractant-composition may include one or more insect sterilants that sterilize the trapped insects or otherwise block their reproductive capacity, thereby reducing the population in the following generation. In some situations allowing, the sterilized insects to survive and compete with non-trapped insects for mates is more effective than killing them outright.

According to another embodiment of the invention, the attractant-composition may include one or more additives that enhance the stability of the composition. Examples of additives include, but are not limited to, fatty acids and vegetable oils, such as for example olive oil, soybean oil, corn oil, safflower oil, canola oil, and combinations thereof.

Furthermore, according to another embodiment of the invention, the attractant-composition may include one or more fillers. Examples of fillers include, but are not limited to, one or more mineral clays (e.g., attapulgite). In some embodiments, the attractant-composition may include one or more organic thickeners. Examples of such thickeners include, but are not limited to, methyl cellulose, ethyl cellulose, and any combinations thereof.

According to another embodiment, the attractant-compositions of the present invention include one or more solvents. Compositions containing solvents are desirable when a user is to employ liquid compositions which may be applied by brushing, dipping, rolling, spraying, or otherwise applying the liquid compositions to substrates on which the user wishes to provide an insecticidal coating. In some embodiments, the solvent(s) to be used in the instant invention is/are selected so as to solubilize, or substantially solubilize, the one or more ingredients of the attractant-composition. Examples of solvents include, but are not limited to, ethyl alcohol, methyl alcohol, chlorinated hydrocarbons, petroleum solvents, turpentine, xylene, and any combinations thereof.

According to another embodiment of the invention, the attractant-composition may include one or more binders, such as synthetic and natural resins typically used in paints and coatings. These may be modified to cause the coated surface to be friable enough to allow insects to bit off and ingest the material, while still maintaining the structural integrity of the coating. In some embodiments, the binder also acts a filler and/or a thickener. Examples of binders include, but are not limited to, one or more of shellac, acrylics, epoxies, alkyds, polyurethanes, linseed oil, tung oil, and any combinations thereof.

The attractant-compositions of the invention may be used in traps, such as those commonly used to attract noctuid moths such as beet army worm and tobacco bud worm. Such traps are well known to one skilled in the art, and are commonly used in many states and countries in their moth eradication programs. In one embodiment, the trap includes one or more septa, containers or storage receptacles for holding the attractant-composition. In some embodiments, the pheromone traps containing the attractant-composition may be combined with other kinds of trapping mechanisms. For example, in addition to the attractant-composition, the pheromone trap may include one or more florescent lights, one or more sticky substrates and/or one or more colored surfaces for attracting noctuid moths. In other embodiments, the pheromone trap containing the attractant-composition may not have other kinds of trapping mechanisms. In particular embodiments, the trap is a Tedders trap (See e.g., Stansly et al., Proc. Fla. State Hort. Soc. 110: 22-26 (1997)) or a Florida trap (See e.g., Mizell and Tedders, Proc. Southeast Pecan Growers Assoc. 90: 52-53) as known to one skilled in art.

A plurality of traps containing the attractant-composition may be placed in a crop field. The locations of the traps, and the height of the traps from ground may be selected in accordance with methods known to one skilled in the art.

The attractant-composition attracts noctuid moths. In one embodiment, the attractant-composition attracts insects of one or more species of the genus *Spodoptera*. In one particular embodiment, the attractant-composition attracts *Spodoptera exigua*. In another embodiment, the attractant-composition attracts insects of one or more species of the genus *Heliothis*. In another particular embodiment, the attractant-composition attracts *Heliothis virescens*.

The invention also provides a method for attracting and trapping noctuid moths. The method includes administering to a predetermined site an effective amount of the attractant-composition. Such administering may be performed by adding the attractant-composition to a septa or storage receptacle of a trap described herein. The trap may be set at any time of the year in a field. Those of skill in the an can readily determine an appropriate amount of the compositions to use in a particular trap, and can also determine an appropriate density of traps/acre of crop field to be protected.

The method may include periodically monitoring the total number or quantity of the trapped insects. The monitoring may be performed by counting the number of insects trapped for a predetermined period of time such as, for example, daily, weekly, bi-weekly, monthly, once-in-three months, or any other time periods selected by the monitor. Such monitoring of the trapped insects may help estimate the population of insects for that particular period, and thereby help determine a particular type and/or dosage of pest control in an integrated pest management system. For example, when the number of trapped noctuid moths is more than a pre-determined level in a particular week, a chemical pesticide may be sprayed or applied to a crop field in order to control noctuid moths or a higher concentration of traps/acre may be set in a crop field in order to control noctuid moths during that particular week.

In some embodiments, the method includes adding a pesticide to the trap so as to kill the trapped noctuid moths. The pesticide may be a pesticide known to one skilled in the art. The pesticide may be mixed with the attractant-composition or may be separately present in a trap. Mixtures may perform the dual function of attracting and killing the noctuid moths.

The attractant-composition may be used in the fields of any crop plants. Examples of such crop plants include, but are not limited to, cotton, corn, soybean, and various vegetable crops.

The following examples are provided to further illustrate the invention described herein.

EXAMPLES

Example 1

*Heliothis Virescens* Response to a Pheromone Synergist

An experiment was carried out near Monticello, Drew County in Arkansas to study the response of tobacco bud worm, *Heliothis virescens* to a pheromone synergist. The experiment was carried out in a habitat of cotton and soybean. β-caryophyllene was used as a synergist with a mixture of pheromones (Z,E)-9,12-tetradecadien-1-ol acetate and (Z)-9-tetradecen-1-ol acetate at the ratio of 7:3. Tedders traps were used in the experiment. Each pheromone trap was baited with the pheromone mixture and approximately 3-6 mg of β-caryophyllene and each control trap was baited with the pheromone mixture. The control trap contained no β-caryophyllene or other synergists. The pheromone mixture used in the experiment was LURETAPE® obtained from Hercon Environmental in Emigsville, Pa. The trapped adult insects of *Heliothis virescens* were collected on a daily basis and the total number of trapped insects was counted. Statistical analysis was done using the Least Squares means separation from the SAS GLM procedure.

FIG. 1 illustrates the average number of moths trapped per day in year 2005. As illustrated in FIG. 1, there was about a 131% increase in the number of captured *Heliothis virescens* when β-caryophyllene was used as a synergist. The observed increase in captured moths was statistically significant at Pr>t 0.01 (1,106 df).

Figure 2:
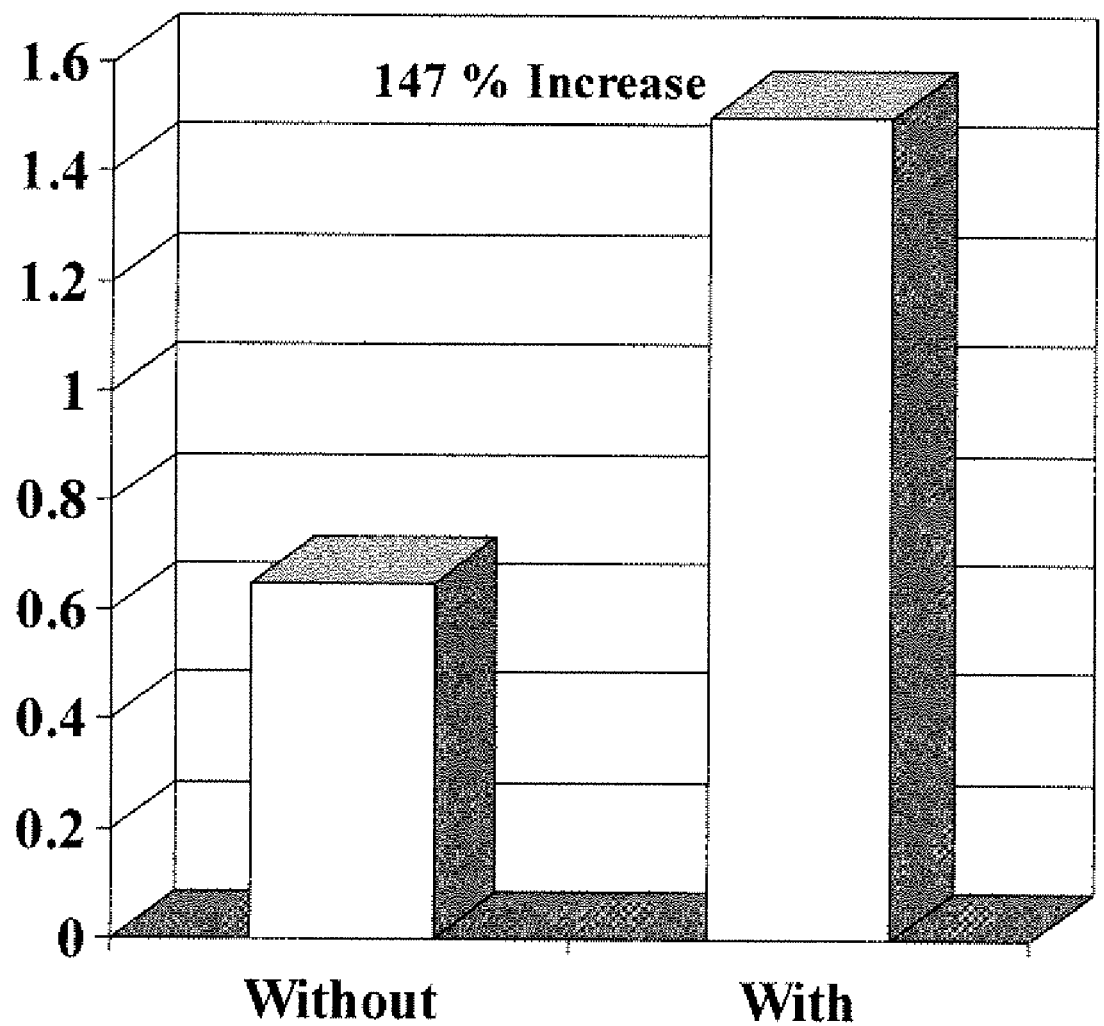
FIG. 2 illustrates a response of *Heliothis virescens* in a cotton environment to pheromone compositions with and without β-caryophyllene as a synergist in year 2004.

FIG. 2 illustrates the average number of moths trapped per day in year 2004. As illustrated in FIG. 2, there was about a 147% increase in the number of captured *Heliothis virescens* when β-caryophyllene was used as a synergist. The observed increase in captured moths was statistically significant at Pr>t 0.23 (2,48 df).

Accordingly, a mixture of pheromones (Z,E)-9,12-tetradecadien-1-ol acetate and (Z)-9-tetradecen-1-ol acetate, when used with β-caryophyllene, significantly improved the trap captures. Thus, β-caryophyllene acts as a synergist with the mixture to attract *Heliothis virescens*.

Example 2

*Spodoptera Exigua* Response to a Pheromone Synergist

An experiment was carried out in three locations in Arkansas to study the response of beet army worm, *Spodoptera exigua*, in a cotton field to a pheromone synergist. The locations were near Fayetteville, Washington County, near Tillar, Drew County, and near Foreman. Little River County. β-caryophyllene was used as a synergist with (Z)-11-hexadecen-1-ol, a pheromone for *Spodoptera exigua*. Tedders traps were used in the experiment. Each pheromone trap was baited with (Z)-11-hexadecen-1-ol and approximately 3-6 mg of β-caryophyllene and each control trap was baited with (Z)-11-hexadecen-1-ol. The control trap contained no β-caryophyllene or other synergists. The trapped adult insects of *Spodoptera exigua* were collected on a daily basis and the total number of trapped insects was counted. Statistical analysis was done using the Least Squares means separation from the SAS GLM procedure.

Figure 3:
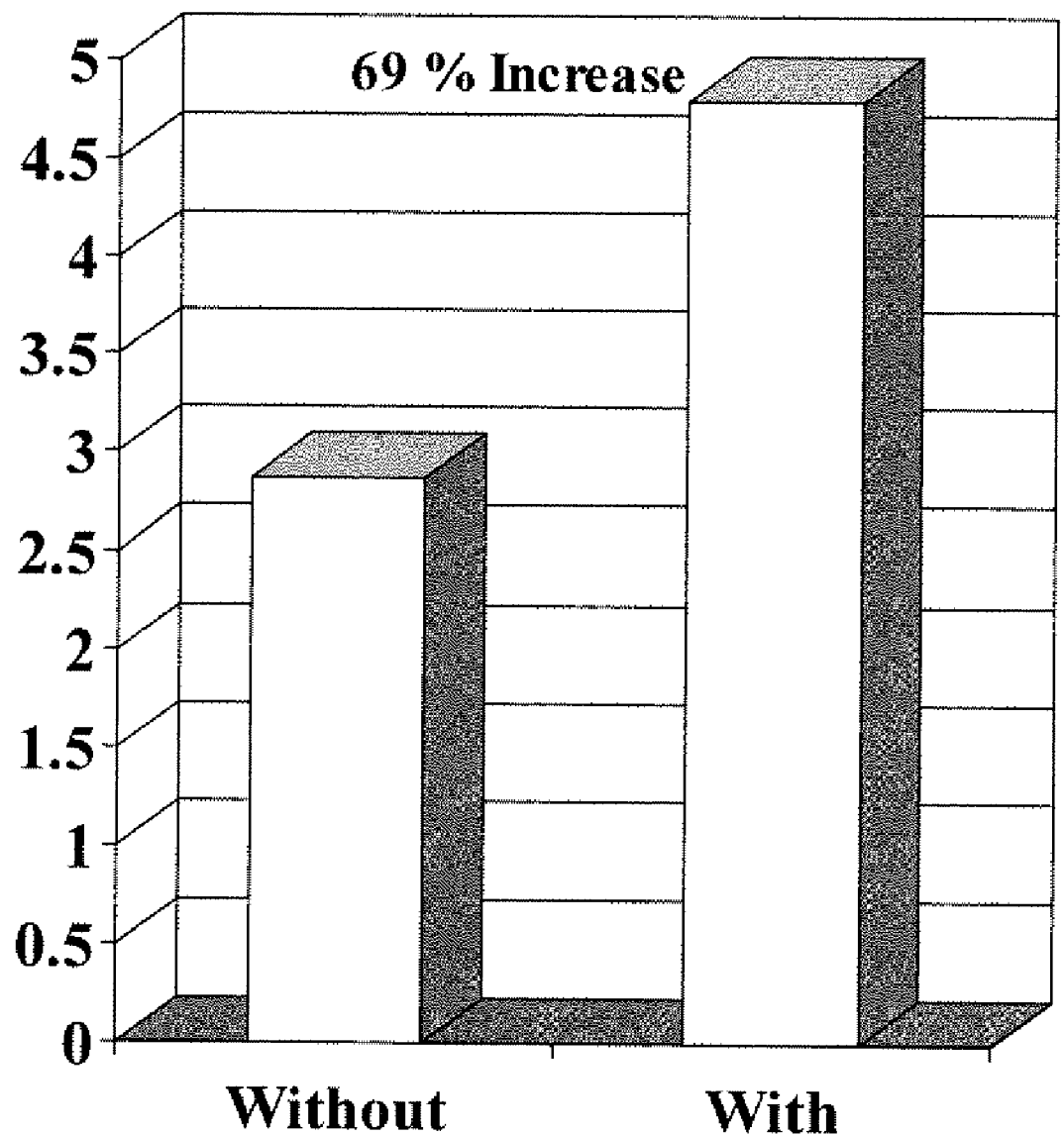
FIG. 3 illustrates a response of *Spodoptera exigua* in a cotton environment to pheromone compositions with and without β-caryophyllene as a synergist in year 2005.

FIG. 3 illustrates the average number of moths trapped per day in year 2005. As illustrated in FIG. 3, there was about a 69% increase in the number of captured *Spodoptera exigua* when β-caryophyllene was used as a synergist. The observed increase in captured moths was statistically significant at Pr>t 0.01 (1,63 df).

Figure 4:
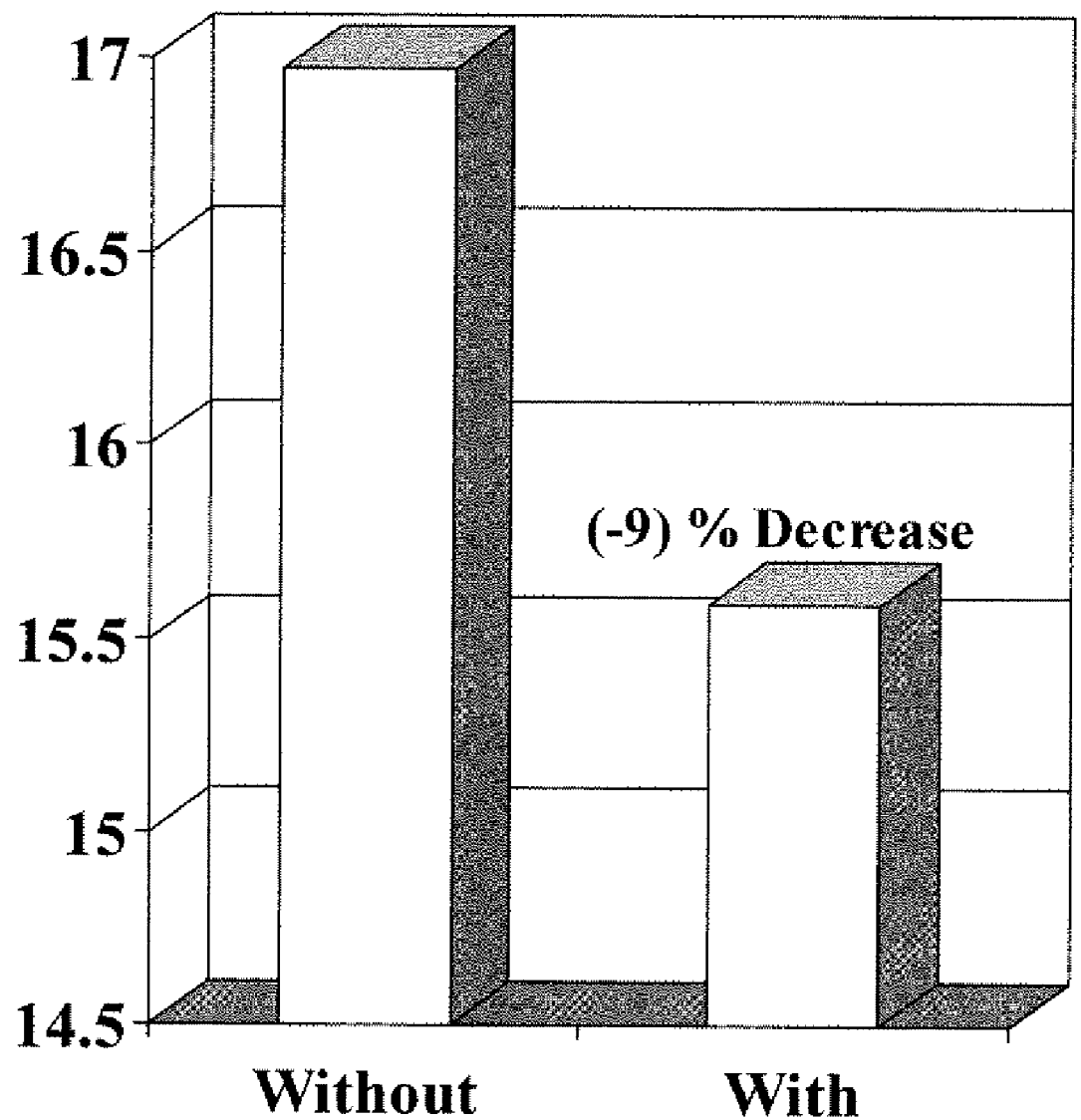
FIG. 4 illustrates a response of *Spodoptera exigua* in a cotton environment to pheromone compositions with and without β-caryophyllene as a synergist in year 2004.

FIG. 4 illustrates the average number of moths trapped per day in year 2004. As illustrated in FIG. 4, there was about a −9% decrease in the number of captu red *Spodoptera exigua* when β-caryophyllene was used as a synergist. This decrease may possibly be due to unknown interacting environmental factors in year 2004.

As per year 2005 data illustrated in FIG. 3, the pheromone, (Z)-11-hexadecen-1-ol, when used with β-caryophyllene, significantly improved the trap captures. Thus, in certain conditions, (Z)-11-hexadecen-1-ol acts synergistically with β-caryophyllene to attract *Spodoptera exigua*.

All publications and patents cited above are hereby incorporated by reference.

What is claimed is:

1. A composition comprising: at least one pheromone compound that attracts at least one species of the family Noctuidae; and purified-β-caryophyllene.

2. The composition of claim 1, wherein said at least one species is *Heliothis virescens*.

3. The composition of claim 2, wherein said at least one pheromone compound is selected from the group comprising (Z,E)-9,12-tetradecadien-1-ol acetate and (Z)-9-tetradecen-1-ol acetate.

4. The composition of claim 2, wherein said at least one pheromone compound is a mixture of (Z,E)-9,12-tetradecadien-1-ol acetate and (Z)-9-tetradecen-1-ol acetate.

5. The composition of claim 4, wherein the ratio of (Z,E)-9,12-tetradecadien-1-ol acetate and (Z)-9-tetradecen-1-ol acetate in the mixture is 7:3.

6. The composition of claim 1, wherein said at least one species is *Spodoptera exigua*.

7. The composition of claim 6, wherein said at least one pheromone compound is (Z)-11-hexadecen-1-ol.

8. The composition of claim 1, wherein the concentration of β-caryophyllene ranges from about 1 mg to about 20 mg.

9. The composition of claim 1, wherein the concentration of β-caryophyllene ranges from about 3 mg to about 6 mg.

10. The composition of claim 1, wherein the concentration of β-caryophyllene is about 1, 2, 3, 5, 6, 7.5, 10, 15, 25, 50, 100 or 200 mg.

11. The composition of claim 1, wherein the composition further comprises a pesticide.

12. The composition of claim 1, wherein the composition further comprises dimilin.

13. The composition of claim 1, wherein the composition further comprises an insect sterilant.

14. The composition of claim 1, wherein the composition is in the form of pellets, microspeheres, nanoparticles or tubules.

15. The composition of claim 1, further comprising, iso-caryophyllene or α-humulene.

16. A composition for attracting at least one species of noctuid moth comprising: at least one pheromone compound comprising a mixture of (Z,E)-9,12-tetradecadien-1-ol acetate and (Z)-9-tetradecen-1-ol acetate, said composition further comprising β-caryophyllene.

17. A trap for capturing an insect of the family Noctuidae, the trap comprising: at least one storage receptacle comprising a composition according to claim 1.

18. A method for controlling at least one species of the family Noctuidae comprising: administering to a predetermined site an effective amount of a composition according to claim 1.

19. The method of claim 18, further comprising periodically monitoring said at least one species of the family Noctuidae captured at the predetermined site.

20. The method of claim 19, the step of monitoring comprising collecting the captured said at least one species of the family Noctuidae at the predetermined site and counting the total number of the captured moths.

21. The method of claim 18, wherein said at least one species of the family Noctuidae is *Spodoptera exigua*.

22. The method of claim 21, wherein said at least one pheromone compound is selected from the group comprising (Z,E)-9,12-tetradecadien-1-ol acetate and (Z)-9-tetradecen-1-ol acetate.

23. The method of claim 21, wherein said at least one pheromone compound is a mixture of (Z,E)-9,12-tetradecadien-1-ol acetate and (Z)-9-tetradecen-1-ol acetate.

24. The composition of claim 23, wherein the ratio of (Z,E)-9,12-tetradecadien-1-ol acetate and (Z)-9-tetradecen-1-ol acetate in the mixture is 7:3.

25. The method of claim 18, wherein said at least one species is *Heliothis virescens*.

26. The method of claim 25, wherein said at least one pheromone compound is (Z)-11-hexadecen-1-ol.

27. The method of claim 18, wherein the concentration of β-caryophyllene ranges from about 1 mg to about 20 mg.

28. The method of claim 18, wherein the concentration of β-caryophyllene ranges from about 3 mg to about 6 mg.

29. The method of claim 18, wherein the concentration of β-caryophyllene is about 1, 2, 3, 5, 6, 7.5, 10, 15, 25, 50, 100 or 200 mg.

30. The method of claim 18, wherein the composition further comprises a pesticide.

31. The method of claim 18, wherein the composition further comprises dimilin.

32. The method of claim 18, wherein the composition further comprises an insect sterilant.

33. The method of claim 18, wherein the composition is in the form of pellets, microspeheres, nanoparticles or tubules.

34. The method of claim 18, wherein the predetermined site is a field having a cotton crop.

* * * * *